(12) United States Patent
Davenport et al.

(10) Patent No.: US 11,058,554 B2
(45) Date of Patent: Jul. 13, 2021

(54) HARD BEARING INSERTER RINGS

(71) Applicant: Biomet Manufacturing, LLC, Warsaw, IN (US)

(72) Inventors: Austen Davenport, Columbia City, IN (US); Stephanie Klunk, Hamilton, OH (US)

(73) Assignee: Biomet Manufacturing, LLC, Warsaw, IN (US)

(*) Notice: Subject to any disclaimer, the term of this patent is extended or adjusted under 35 U.S.C. 154(b) by 67 days.

(21) Appl. No.: 15/098,870

(22) Filed: Apr. 14, 2016

(65) Prior Publication Data

US 2016/0302944 A1 Oct. 20, 2016

Related U.S. Application Data

(60) Provisional application No. 62/148,786, filed on Apr. 17, 2015.

(51) Int. Cl.
*A61F 2/36* (2006.01)
*A61F 2/30* (2006.01)
(Continued)

(52) U.S. Cl.
CPC .............. *A61F 2/4609* (2013.01); *A61F 2/34* (2013.01); *A61F 2/4637* (2013.01);
(Continued)

(58) Field of Classification Search
CPC .. A61F 2/34; A61F 2/4609; A61F 2/32; A61F 2220/0025; A61F 2002/30332;
(Continued)

(56) References Cited

U.S. PATENT DOCUMENTS

| 4,718,911 A | 1/1988 | Kenna |
| 4,919,674 A * | 4/1990 | Schelhas .................. A61F 2/34 |
| | | 623/22.29 |

(Continued)

FOREIGN PATENT DOCUMENTS

| CN | 201182659 Y | 1/2009 |
| CN | 107920899 A | 4/2018 |

(Continued)

OTHER PUBLICATIONS

"International Application Serial No. PCT/US2016/027489, International Search Report dated Jul. 29, 2016", 6 pgs.

(Continued)

*Primary Examiner* — Ann Schillinger
(74) *Attorney, Agent, or Firm* — Schwegman Lundberg & Woessner, P.A.

(57) ABSTRACT

A fitting ring can be provided that is attachable to an edge of a liner for an acetabular shell. The fitting ring can include an alignment portion shaped or configured to engage a lip portion of the acetabular shell as the liner is inserted into the acetabular shell to center the liner and correct any pivoting of the liner relative to the acetabular shell. A driving force can be applied to the liner to drive the liner into the acetabular shell while the fitting ring guides the liner as the liner is inserted into the acetabular shell. Driving the liner into the acetabular shell can also cause the fitting ring to disengage from the liner.

15 Claims, 7 Drawing Sheets

(51) Int. Cl.
*A61F 2/34* (2006.01)
*A61F 2/46* (2006.01)
*A61F 2/32* (2006.01)

(52) U.S. Cl.
CPC ... *A61F 2002/302* (2013.01); *A61F 2002/305* (2013.01); *A61F 2002/30495* (2013.01); *A61F 2002/3241* (2013.01); *A61F 2002/4641* (2013.01); *A61F 2002/4681* (2013.01)

(58) Field of Classification Search
CPC .... A61F 2002/30364; A61F 2002/3291; A61F 2002/30616; A61F 2002/3241
See application file for complete search history.

(56) References Cited

U.S. PATENT DOCUMENTS

| | | | | |
|---|---|---|---|---|
| 4,969,910 | A | * | 11/1990 | Frey ............... A61F 2/30907 623/22.33 |
| 5,002,577 | A | | 3/1991 | Bolesky et al. |
| 5,314,491 | A | * | 5/1994 | Thongpreda ............ A61F 2/32 623/22.29 |
| 5,824,108 | A | * | 10/1998 | Huebner ............... F16C 11/069 623/22.29 |
| 5,989,293 | A | * | 11/1999 | Cook .................. A61F 2/32 623/22.29 |
| 2006/0004463 | A1 | * | 1/2006 | Lewis ................. A61F 2/32 623/22.38 |
| 2006/0241781 | A1 | | 10/2006 | Brown et al. |
| 2007/0219640 | A1 | | 9/2007 | Steinberg |
| 2007/0239283 | A1 | * | 10/2007 | Berger ............... A61F 2/30721 623/22.29 |
| 2011/0245837 | A1 | | 10/2011 | Preuss et al. |

FOREIGN PATENT DOCUMENTS

| | | |
|---|---|---|
| DE | 19820721 A1 | 11/1999 |
| DE | 102009054633 A1 | 6/2010 |
| EP | 0234811 A1 | 9/1987 |
| EP | 0315795 A1 | 5/1989 |
| EP | 1205165 A1 | 5/2002 |
| WO | WO-2008106598 A1 | 9/2008 |
| WO | WO-2011161166 A1 | 12/2011 |
| WO | WO-2016168434 A1 | 10/2016 |
| WO | WO-2017014625 A1 | 1/2017 |

OTHER PUBLICATIONS

"International Application Serial No. PCT/US2016/027489, Written Opinion dated Jul. 29, 2016", 7 pgs.

"European Application Serial No. 16717820.1, Communication Pursuant to Article 94(3) EPC dated Aug. 29, 2018", 5 pgs.

"European Application Serial No. 16717820.1, Response dated Jun. 26, 2018 to Office Action dated Dec. 21, 2018", 17 pgs.

"European Application Serial No. 16717820.1, Response dated Mar. 8, 2019 to Communication Pursuant to Article 94(3) EPC dated Aug. 29, 2018", 19 pgs.

"Chinese Application Serial No. 201680029462.3, Response dated Mar. 14, 2019 to Office Action dated Dec. 26, 2018", w English Claims, 9 pgs.

"Chinese Application Serial No. 201680029462.3, Office Action dated Dec. 26, 2018", (W/ English Translation), 12 pgs.

"Chinese Application Serial No. 201680029462.3, Office Action dated Jul. 24, 2019", (W/ English translation), 8 pgs.

"Chinese Application Serial No. 201680029462.3, Response dated Sep. 20, 2019 to Office Action dated Jul. 24, 2019", (W/ English claims), 10 pgs.

"European Application Serial No. 19202108.7, Extended European Search Report dated Oct. 9, 2020", 8 pgs.

* cited by examiner

HARD BEARING INSERTER RINGS

CLAIM OF PRIORITY

This patent application claims the benefit of priority, under 35 U.S.C. Section 119(e), to Austen Davenport et al. U.S. patent application Ser. No. 62/148,786, entitled "Hard Bearing Inserter Rings," filed on Apr. 17, 2015, each of which is hereby incorporated by reference herein in its entirety.

TECHNICAL FIELD

This document pertains generally, but not by way of limitation, to fitting a liner to an acetabular shell for hip replacement or revision surgery.

BACKGROUND

In a hip replacement or revision surgery, the acetabulum of the hip is reamed to provide a socket shaped mounting surface corresponding to the size and curvature of the femoral head of the natural or revised femur or femoral implant. After the prepared mounting surface is appropriately sized and shaped, an acetabular shell can be mounted to the mounting surface to provide a bearing surface for the femoral head. The acetabular shell can comprise a hemispherical shape to define a socket for receiving the femoral head. A liner can be inserted into the acetabular shell to fit the liner to an inner surface of the acetabular shell to cover mounting features or textures to provide a smooth bearing surface against which the femoral head can smoothly articulate.

The liner can often comprise a rigid or a resilient flexible material for withstanding the articulation of the femoral head, which requires the liner to be driven into the acetabular shell. If the liner is not properly aligned or centered with the acetabular shell prior to insertion, the liner can be improperly seated within the acetabular shell after insertion. A properly fitted liner is flush or nearly flush with the lip of the acetabular shell to avoid providing an edge or other protrusion that extends from the acetabular shell. The rigid or resilient flexible material of the liner requires the liner to be pried from the acetabular shell if improperly seated. The locking mechanism of the liner and the acetabular shell can make the liner difficult to pry from the acetabular shell. In addition, as the opening in the tissue to access the hip bone is usually minimally sized to reduce healing time, accessing the implanted acetabular shell and liner can be difficult causing discomfort or pain to the patient.

The inner surface of the acetabular shell can often have a curvature that corresponds to the outer surface of the acetabular shell. Acetabular shells commonly have a tapered region extending from the lip of the acetabular shell to the inner surface providing a thinner lip portion and corresponding to different bearing materials. While the tapered region provides an advantageous structure for the acetabular shell, the tapered region can make centering or aligning the liner more difficult and provide an angled surface that can cause the liner to shift or pivot as the liner is inserted into the acetabular shell.

OVERVIEW

The present inventors have recognized, among other things, that a problem to be solved can include the insertion of a liner into an acetabular shell at the proper alignment to avoid increasing the length of the surgical procedure or discomfort to the patient. In an example, the present subject matter can provide a solution to this problem, such as by attaching a fitting ring to an edge of a liner such that an alignment portion of the fitting ring extends radially outward from the liner. The alignment portion is shaped or configured to engage a lip portion of an acetabular shell as the liner is inserted into the acetabular shell. The engagement of the fitting ring to the lip portion of the acetabular shell centers the liner and corrects any pivoting of the liner relative to the acetabular shell. A driving force can be applied to the liner to drive the liner into the acetabular shell where the fitting ring guides the liner as the liner is inserted into the acetabular shell. Driving the liner into the acetabular shell can also cause the fitting ring to disengage from the liner.

A method for installing an acetabular implant can include reaming the acetabulum to prepare a curved mounting surface and fixing an outer surface of an acetabular shell to the mounting surface. The method can further include providing a liner and attaching a fitting ring to an edge portion of the liner such that an alignment feature of the fitting ring extends radially outward from the liner. The method can further include inserting the liner into an opening of the acetabular shell such that the liner is positioned adjacent to an inner surface of the acetabular shell. The insertion of the liner engages the alignment feature of the fitting ring to a lip portion of the acetabular shell defining the opening, where the fitting ring centers and corrects pivoting of the liner relative to the acetabular shell. The method can further include driving the liner into the acetabular shell such that the liner engages the inner surface of the acetabular shell and disengage the fitting ring from the liner.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As depicted in FIGS. 1-2 and 5A-5C, an acetabular implant system 20, according to an example of the present disclosure, can include an acetabular shell 22, a liner 24, and a fitting ring 26. The acetabular shell 22 can be mounted to a prepared mounting surface on an acetabulum of the hip joint. The liner 24 can be fitted to the acetabular shell 22 to provide a bearing surface for a femoral head of a natural or resected femur or a femoral implant. The fitting ring 26 can be engaged to the liner 24 such that inserting the liner 24 into the acetabular shell 22 engages the fitting ring 26 to the acetabular shell 22 to center the liner 24 and correct any pivoting of the liner 24 with respect to the acetabular shell 22.

The acetabular shell 22 can comprise an outer surface 28 and an inner surface 30. The outer surface 28 can be textured, shaped, perforated or include mounting features for receiving fasteners, cement, and/or bone in-growth material to fix the acetabular shell 22 to the acetabulum of the hip. The acetabular shell 22 can comprise a generally hemispherical shape such that the inner surface 30 is curved to an apex 32 to define a socket space for receiving a femoral head of a femur or a femoral implant. The acetabular shell 22 can include a lip portion 34 (see FIG. 5a) defining a generally circular opening for accessing the socket space defined by the inner surface 30. In an example, the acetabular shell 22 can include a tapered portion 36 extending from the lip portion 34 to the inner surface 30 and can have a different curvature from the inner surface 30. The inner surface 30 can have a curvature corresponding to the curvature of the outer surface 28. The tapered portion 36 can have a different curvature from the inner surface 30. In an example, the acetabular shells can have a diameter from about 40 mm to about 80 mm.

The liner 24 can comprise a bearing surface 38 and an edge portion 40 extending around the bearing surface 38. The liner 24 can comprise a generally hemispherical shape such that the bearing surface 38 is curved to define a socket space for receiving the femoral head. The liner 24 can be shaped to correspond to the curvature of the inner surface 30 of the acetabular shell 22. The liner 24 can comprise a rigid material, a resilient flexible material, or combinations thereof. In an example, the liner 24 can comprise a polymer, a ceramic, a metal, a composite, or combinations thereof.

Figure 3:
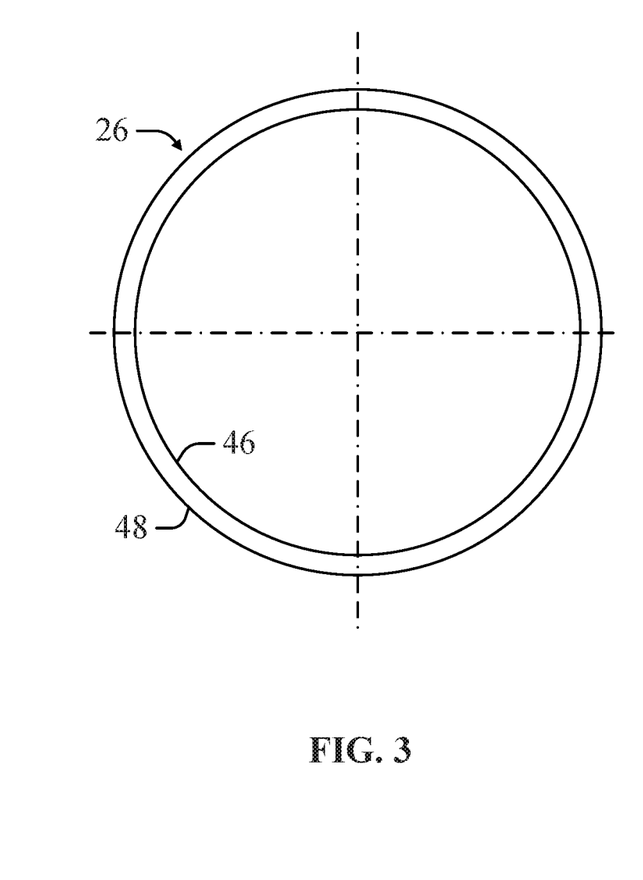
FIG. 3 is a top view of a fitting ring according to an example of the present disclosure.
Figure 4:
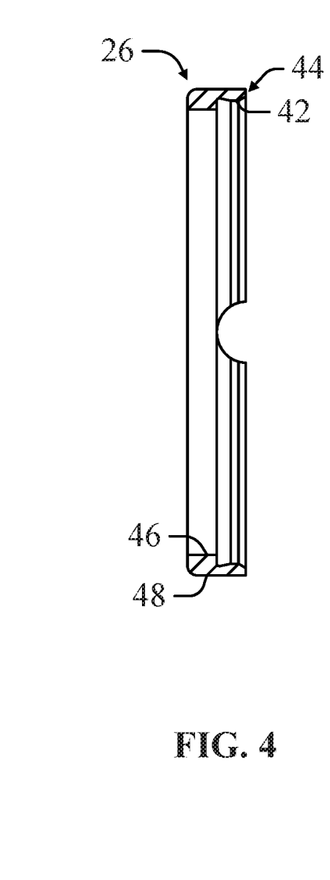
FIG. 4 is a cross-sectional side view of the fitting ring depicted in FIG. 3.

As depicted in FIGS. 3-4, the fitting ring 26 can include an engagement portion 42 and an alignment portion 44. The engagement portion 42 can be positioned on an interior surface 46 of the fitting ring 26. In an example, the engagement portion 42 can include a snap fit feature engageable to an edge portion 40 of the liner 24. The fitting ring 26 can comprise a resilient flexible material including, but not limited to a flexible polymer, a rubber or combinations thereof. In this configuration, the fitting ring 26 can flex to engage the engagement portion 42 to the edge portion 40 of the liner 24. Similarly, the fitting ring 26 can be flexed to disengage the engagement portion 42 from the edge portion 40 of the liner 24. The alignment portion 44 can be positioned on an exterior surface 48 of the fitting ring 26. The alignment portion 44 can be sized such that the alignment portion 44 corresponds to the lip portion 34 of the acetabular shell 22. The fitting ring 26 can have an inner diameter of from about 40 mm to about 80 mm to correspond to the outer diameter of the acetabular shell 22.

Figure 1:
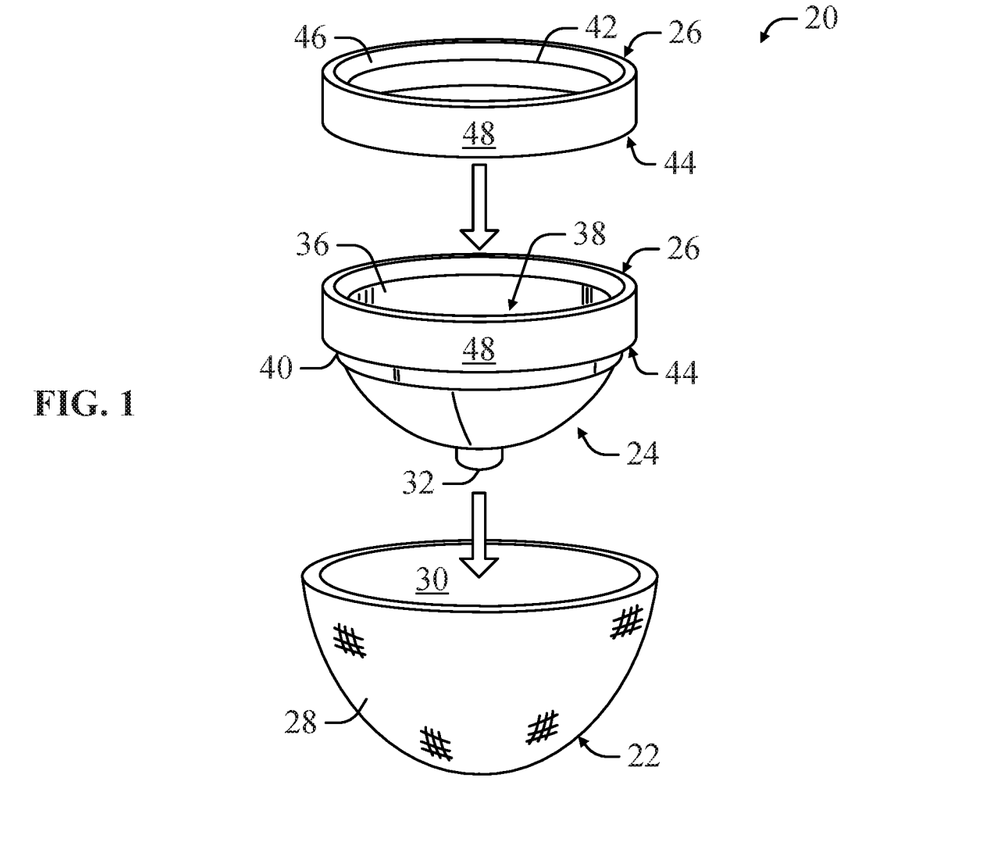
FIG. 1 is a perspective schematic view illustrating attachment of a fitting ring to a liner and insertion of the liner into the acetabular shell according to an example of the present disclosure.
Figure 2:
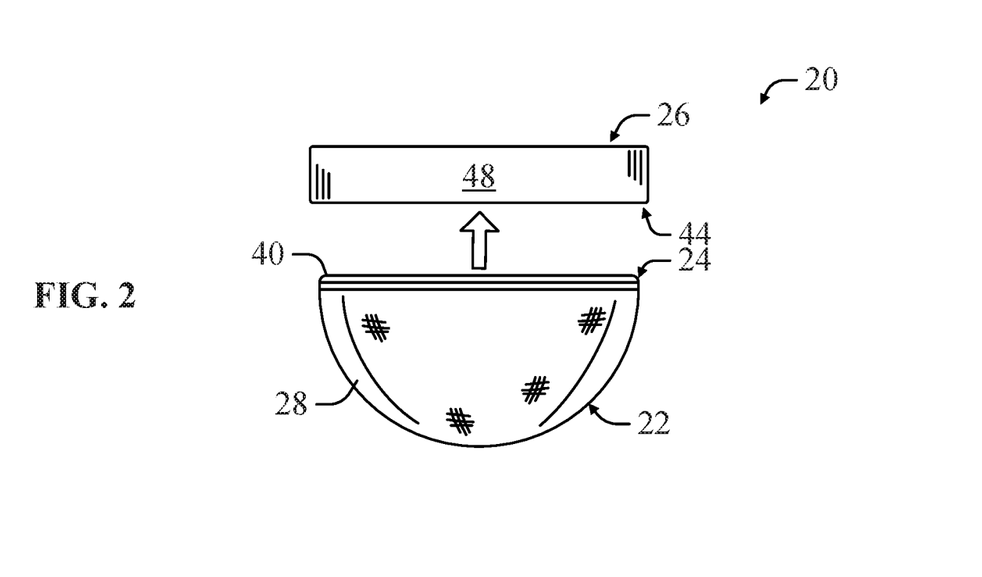
FIG. 2 is a side schematic view illustrating disengagement of a fitting ring from a liner upon insertion of the liner into an acetabular shell according to an example of the present disclosure.
Figure 5A:
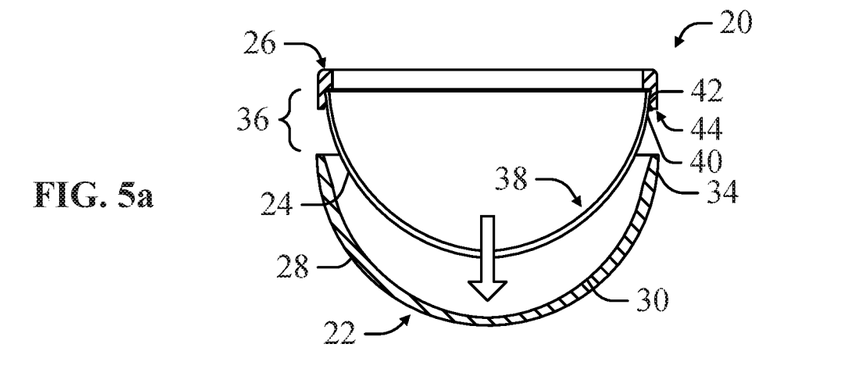
FIG. 5a is a cross-sectional side schematic view illustrating insertion of a liner having an attached fitting ring into an acetabular shell according to an example of the present disclosure.
Figure 5B:
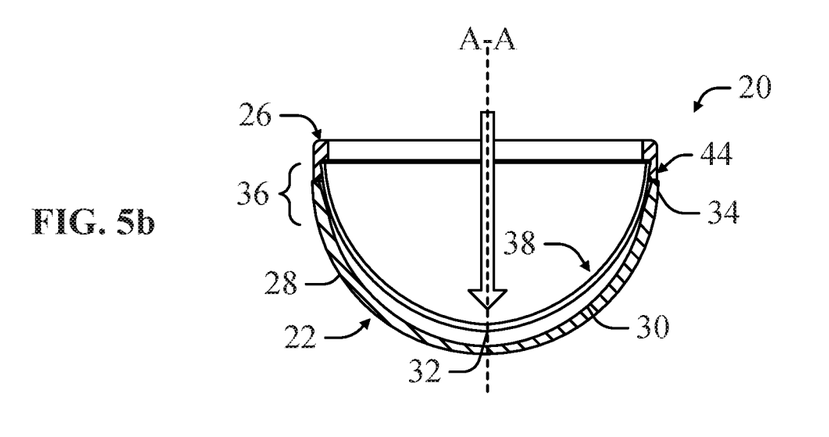
FIG. 5b is a cross-sectional side schematic view illustrating engagement of the attached fitting ring to the acetabular shell to align the liner with the acetabular shell according to an example of the present disclosure.

In operation, the engagement portion 42 of the fitting ring 26 can be attached to the edge portion 40. The fitting ring 26 can be flexed to engage the engagement portion 42 to the liner 24. As depicted in FIGS. 1 and 5a-5b, the engagement portion 42 can extend circumferentially around the interior surface 46 of the fitting ring 26 to evenly engage the entirety of the edge portion 40 of the liner 24. As depicted, the engagement portion 42 is positioned on the fitting ring 26, but it is contemplated that the engagement portion 42 can be positioned on the edge portion 40 of the liner 24 to engage the interior surface 46.

As depicted in FIGS. 5a-5b, the liner 24 can be inserted through the opening defining the lip portion 34. The alignment portion 44 can engage the lip portion 34 as the liner 24 is inserted to maintain the liner 24 at a predetermined distance from the inner surface 30 of the acetabular shell 22. The liner 24 and the alignment portion 44 cooperate to center the liner 24 within the opening of the acetabular shell 22. The alignment portion 44 can engage the circumference of the lip portion 34 to correct any pivoting of the liner 24 relative acetabular shell 22.

Figure 5C:
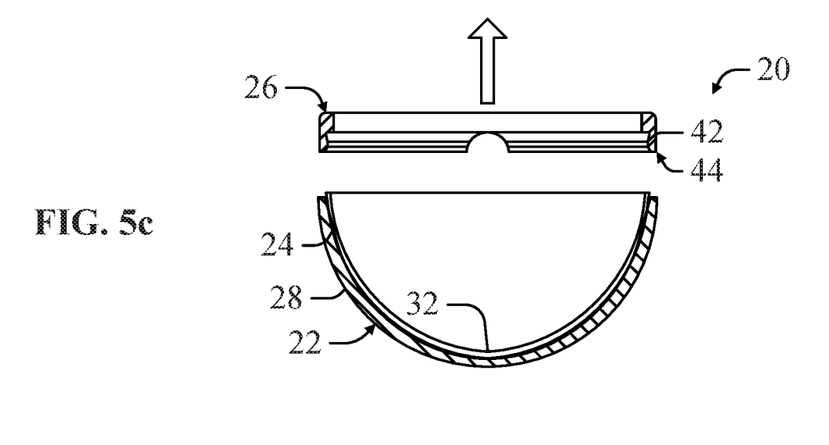
FIG. 5c is a cross-sectional side schematic view illustrating disengagement of the fitting ring from the liner following insertion of the liner into the acetabular shell according to an example of the present disclosure.

As depicted in FIGS. 5b-5c, a driving force can be applied to the liner 24 along an axis A-A traversing the apex 32 of the acetabular shell 22. The fitting ring 26 can be sized and structured to guide the liner 24 as the liner 24 is inserted to avoid pivoting of the liner 24. In an example, the fitting ring 26 flexes as the liner 24 is inserted to disengage the fitting ring 26 from the liner 24.

As depicted in FIGS. 6 and 7-9, a method 100 can comprise site preparation 102, acetabular shell mounting 104, fitting ring attachment 106, liner alignment 108, and liner mounting 110.

Figure 9:
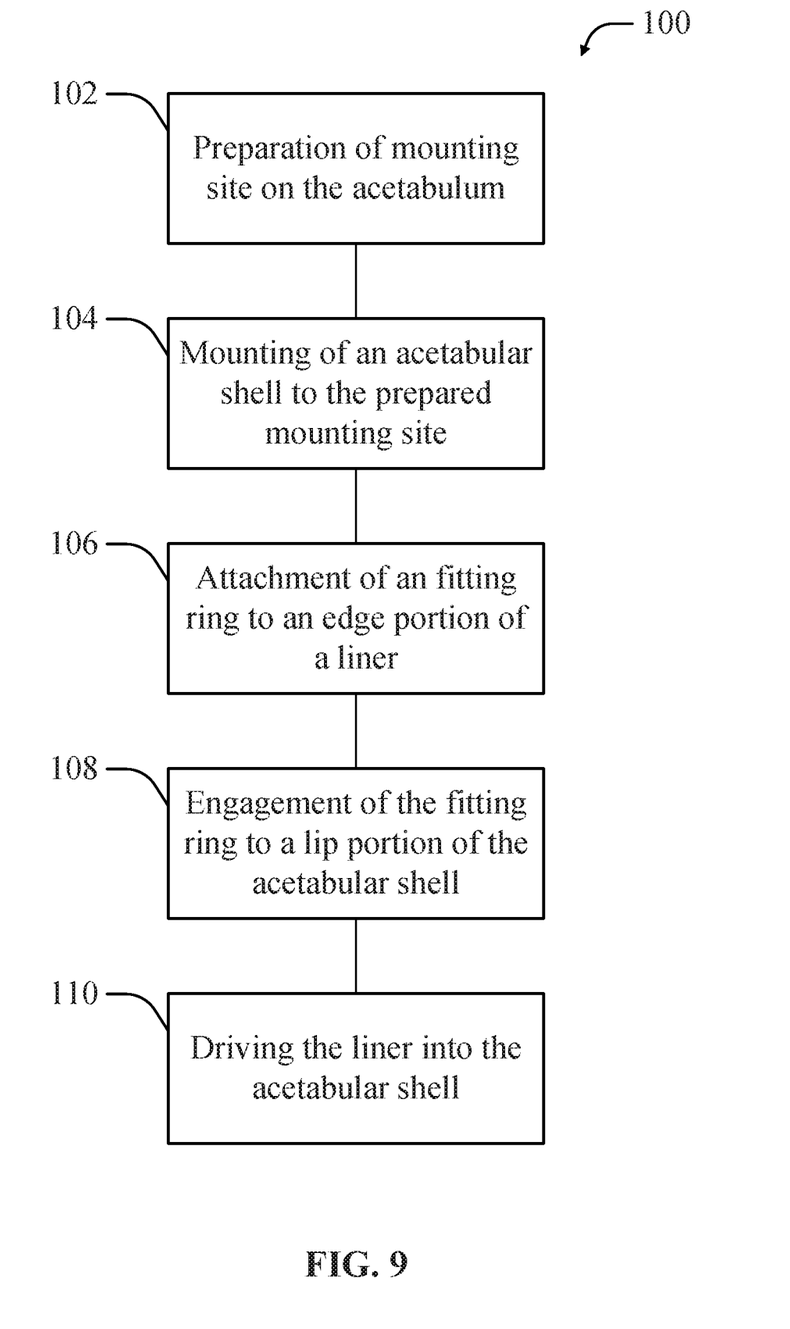
FIG. 9 is a schematic diagram of a method for inserting a liner into an acetabular shell with a fitting ring according to an example of the present disclosure.

In the site preparation step 102, if necessary, a reamer is applied to the acetabulum of a hip at the mounting site to ream the bone. Increasingly sized reamers can be used to enlarge the mounting site and form an acetabular cavity. In an example, the bone can be reamed until bleeding subchondral bone is exposed. The acetabular orientation of the mounting site can be about 40 degrees inclination and about 20 degrees of anteversion, but depends on patient anatomy and the femoral implant and can be varied slightly.

Figure 6:
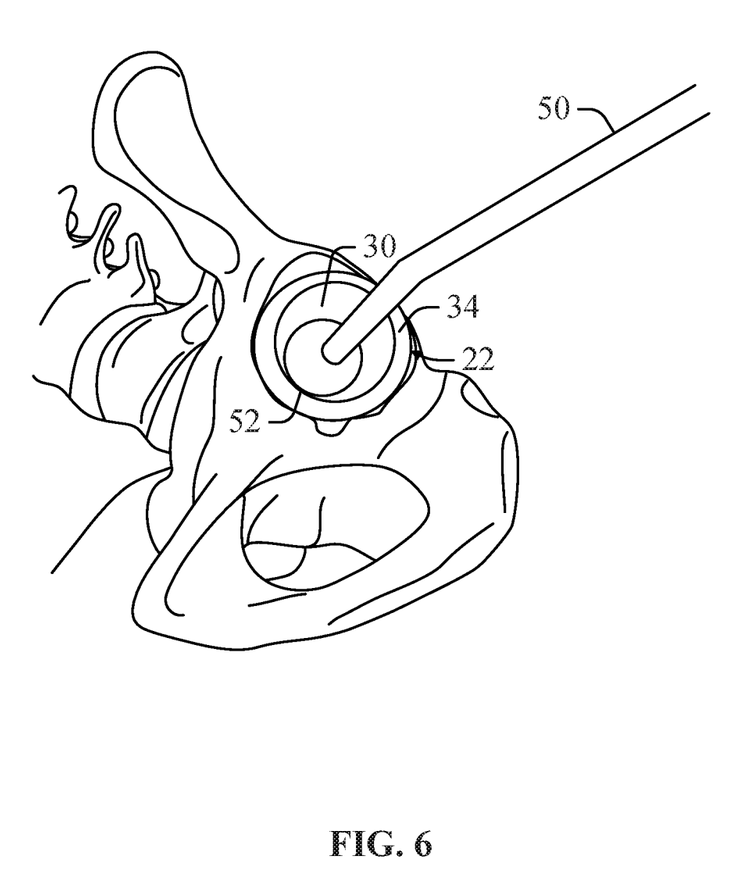
FIG. 6 is a perspective view illustrating insertion of a liner with an attached fitting ring into an acetabular shell according to an example of the present disclosure.

In the acetabular shell mounting step 104, the outer surface 28 of the acetabular shell 22 can be fitted to the mounting surface of the acetabulum. As depicted in FIG. 6, a face impactor plate 52 of an impactor 50 can be fitted to the mounting surface of the acetabulum. The face impactor 52 can be shaped to correspond to the inner surface 30 of the acetabular shell 22. The impactor 50 can be impacted with a hammer to drive the acetabular shell 22 into the mounting surface of the acetabulum. In an example, a cement, a fastener, or another mounting feature can be used to fix the acetabular shell 22 to the mounting surface of the acetabulum.

In the fitting ring attachment step 106, the fitting ring 26 can be flexed to engage the engagement portion 42 to the liner 24 such that the alignment portion 44 of the liner 24 extends radially outward from the liner 24.

Figure 7:
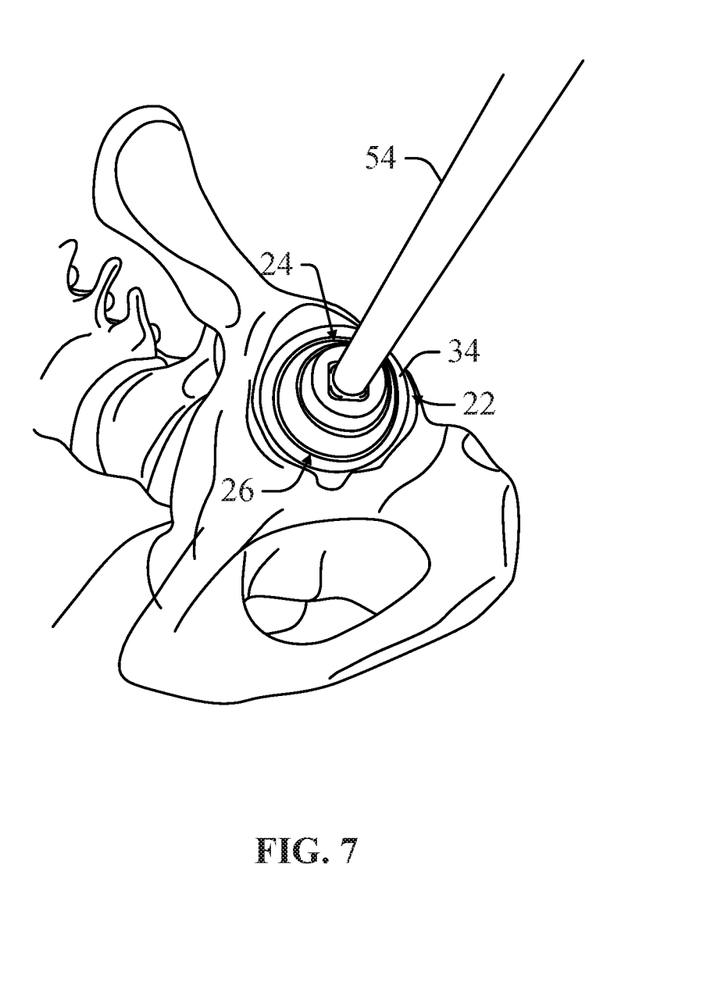
FIG. 7 is a perspective view illustrating engagement of the attached fitting ring depicted in FIG. 6 to the acetabular shell to align the liner with the acetabular shell according to an example of the present disclosure.

As depicted in FIG. 7, in the liner alignment step 108, an inserter 54 can be fitted to the liner 26 and manipulated to insert the liner 26 through the opening of the acetabular shell 22. The insertion of the liner 26 can engage the alignment portion 44 to the lip portion 34 of the acetabular shell 22, which can center the liner 26 within the opening of the acetabular shell 22. The engagement of the alignment portion 44 can also correct the pivoting of the liner 26 of the acetabular shell 22.

Figure 8:
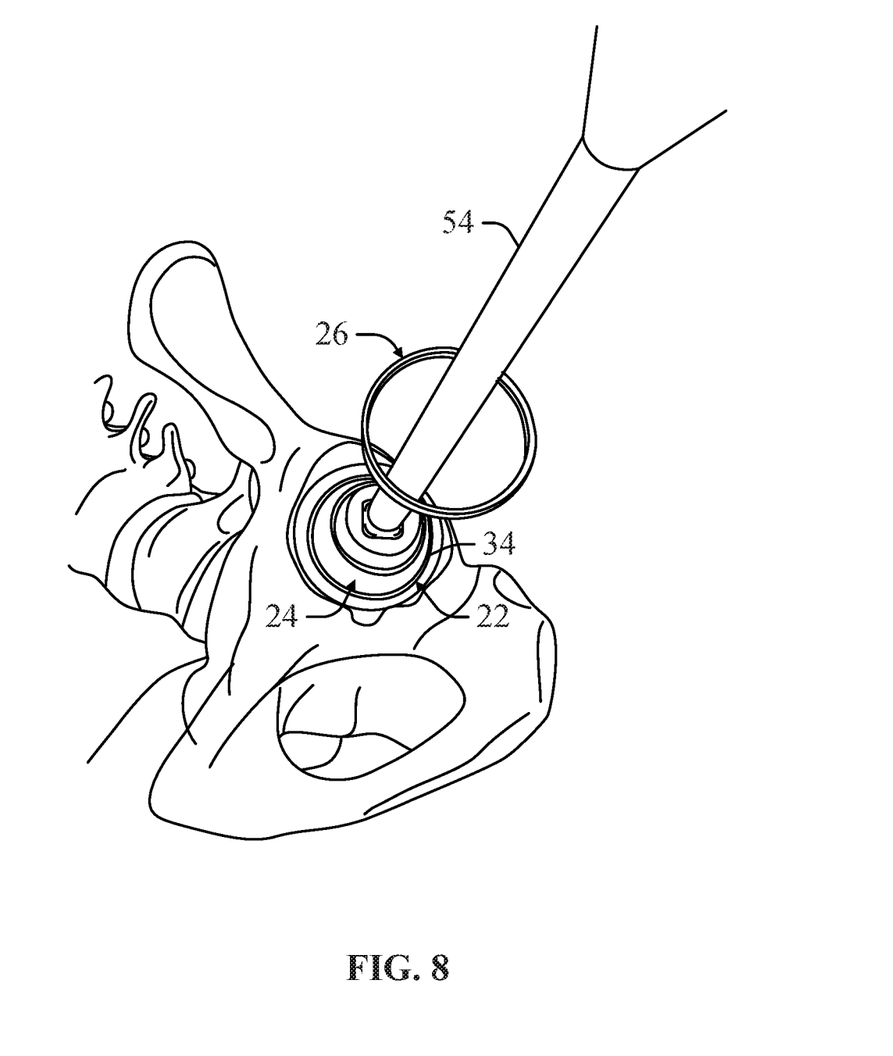
FIG. 8 is a perspective view disengagement of the fitting ring depicted in FIG. 6 from the liner following insertion of the liner into the acetabular shell according to an example of the present disclosure.

As depicted in FIG. 8, in the liner mounting step 110, the inserter 54 can be manipulated to apply a driving force along an axis A-A transverse to the apex 32 of the acetabular shell 22 to push the liner 24 into the acetabular shell 22. The liner 24 can guide the acetabular shell 22 as the liner 24 is driven into acetabular shell 22. The driving force flexes the fitting ring 26 against the acetabular shell 22 to disengage the engagement portion 42 from the liner 24.

VARIOUS NOTES & EXAMPLES

Example 1 is an acetabular implant system, comprising: an acetabular shell including an inner surface and a lip portion defining an opening; a liner having an edge portion; and a fitting ring having an alignment portion and an engagement portion engageable to the edge portion of the liner such that the alignment portion extends radially outward from the liner; wherein the alignment portion is engageable to the lip portion of the acetabular shell to position the liner within the opening at a predetermined distance from the inner surface.

In Example 2, the subject matter of Example 1 optionally includes wherein the acetabular shell comprises a hemispherical shape and the inner surface is centered on an apex of the hemispherical shape.

In Example 3, the subject matter of Example 2 optionally includes wherein applying a driving force along an axis transverse to the apex releases the liner from the fitting ring and pushes the liner into engagement with the inner surface of the acetabular shell.

In Example 4, the subject matter of Example 3 optionally includes wherein the fitting ring comprises a flexible material such that applying the driving force to the liner flexes the engagement portion to release the liner.

In Example 5, the subject matter of Example 4 optionally includes wherein the engagement feature is an annular snap fit feature positioned on an interior surface of the fitting ring.

In Example 6, the subject matter of any one or more of Examples 1-5 optionally include wherein the liner comprises a rigid material.

In Example 7, the subject matter of Example 6 optionally includes wherein the rigid material comprises at least one of a ceramic, a metal, or a composite.

In Example 8, the subject matter of any one or more of Examples 1-7 optionally include wherein a diameter of the fitting ring corresponds to a diameter of the acetabular shell such that the alignment feature engages the lip portion of the acetabular shell when the liner is inserted into the opening.

In Example 9, the subject matter of any one or more of Examples 1-8 optionally include where the acetabular shell includes a taper portion between the inner surface and the lip portion; wherein the taper portion has a different curvature than the inner surface.

Example 10 is a method of implanting an acetabular implant, comprising: fixing an acetabular shell to a mounting surface on an acetabulum, the acetabular shell having an inner surface and a lip portion defining an opening; coupling an engagement portion of a fitting ring to an edge portion of a liner such that an alignment portion of the fitting ring extends radially outward from the liner; and inserting the liner into the opening such that the alignment portion engages the lip portion of the acetabular shell; wherein engaging the alignment portion to the lip portion of the acetabular shell maintains the liner at a predetermined distance from the inner surface.

In Example 11, the subject matter of Example 10 optionally includes applying a driving force to the liner toward the acetabular shell to disengage the liner from the fitting ring and push the liner into engagement with the inner surface of the acetabular shell.

In Example 12, the subject matter of Example 11 optionally includes wherein the acetabular shell comprises a hemispherical shape and the inner surface is centered on an apex of the hemispherical shape; wherein the driving force is applied along an axis transverse to the apex.

In Example 13, the subject matter of any one or more of Examples 11-12 optionally include wherein the fitting ring comprises a flexible material such that applying the driving force to the liner flexes the engagement portion to release the liner.

In Example 14, the subject matter of Example 13 optionally includes wherein the engagement feature is an annular snap fit feature positioned on an interior surface of the fitting ring.

In Example 15, the subject matter of any one or more of Examples 10-14 optionally include wherein the liner comprises a rigid material.

In Example 16, the subject matter of Example 15 optionally includes wherein the rigid material comprises at least one of a ceramic, a metal, or a composite.

Example 17 is a fitting ring for inserting a liner into an acetabular shell, comprising: a fitting ring body including: an alignment portion on an exterior surface, the alignment portion defining extending circumferentially around the fitting ring, and an engagement portion on an interior surface defining an opening for receiving the liner; wherein the alignment portion is engageable to a lip portion of the acetabular shell to position the liner within the opening at a predetermined distance from the inner surface.

In Example 18, the subject matter of Example 17 optionally includes wherein the fitting ring body comprises a flexible material such that applying the driving force to the liner flexes the engagement portion to release the liner.

In Example 19, the subject matter of Example 18 optionally includes wherein the engagement feature is an annular snap fit feature positioned on an interior surface of the fitting ring body.

In Example 20, the subject matter of any one or more of Examples 17-19 optionally include wherein the engagement portion defining extending circumferentially around the fitting ring.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. An acetabular implant system, comprising:
   an acetabular shell comprising a hemispherical shape and including an outer surface, an inner surface centered on an apex of the hemispherical shape, and a lip portion joining the outer and inner surfaces such that the lip portion defines an outermost edge of the acetabular shell, the lip portion further defining an opening of the acetabular shell, the lip portion spaced from the apex by a first distance along a shell axis that extends transverse to the apex;
   a liner having an inner bearing surface and an edge portion, the edge portion including an outer edge surface opposite the inner bearing surface; and
   a fitting ring having an alignment portion and an engagement portion, the engagement portion located on an inner surface of the fitting ring and engageable to the outer edge surface of the liner such that the alignment portion extends radially outward from the edge portion of the liner;
   wherein the engagement portion is an annular snap fit feature positioned on the inner surface of the fitting ring;
   wherein the alignment portion is engageable to the lip portion of the acetabular shell such that the engagement portion is spaced from the apex by a second distance along the shell axis that is greater than the first distance, thereby positioning the liner within the opening at a predetermined, non-zero distance from the inner surface of the acetabular shell at the apex; and
   wherein applying a driving force along the shell axis releases the liner from the fitting ring and pushes the liner into engagement with the inner surface of the acetabular shell at the apex.

2. The acetabular implant system of claim 1, wherein the fitting ring comprises a flexible material such that applying the driving force to the liner flexes the engagement portion to release the liner.

3. The acetabular implant system of claim 1, wherein the liner comprises a rigid material.

4. The acetabular implant system of claim 3, wherein the rigid material comprises at least one of a ceramic, a metal, or a composite.

5. The acetabular implant system of claim 1, wherein a diameter of the fitting ring corresponds to a diameter of the acetabular shell such that the alignment portion engages the lip portion of the acetabular shell when the liner is inserted into the opening.

6. The acetabular implant system of claim 1, where the acetabular shell includes a taper portion between the inner surface and the lip portion;
   wherein the taper portion has a different curvature than the inner surface.

7. An acetabular implant system, comprising:
   an acetabular shell including an inner surface centered on an apex, a lip portion defining an opening of the acetabular shell, and a taper portion between the inner surface and the lip portion, wherein the lip portion defines an outermost edge of the acetabular shell, and wherein the lip portion is spaced from the apex by a first distance along a shell axis that extends transverse to the apex;
   a liner having an inner bearing surface, an outer edge surface opposite the inner bearing surface, and an exterior rim surface separating the inner bearing surface from the outer edge surface and defining an opening of the liner; and
   a fitting ring having an alignment portion and an engagement portion, the engagement portion located on an inner surface of the fitting ring and engageable to the outer edge surface of the liner such that the alignment portion extends radially outward from the outer edge surface of the liner and the fitting ring extends over and radially inward of the exterior rim surface of the liner;
   wherein the engagement portion is a snap fit feature; and wherein the alignment portion is engageable to the lip portion of the acetabular shell such that the engagement portion is spaced from the apex by a second distance along the shell axis that is greater than the first distance, thereby positioning the liner within the opening of the acetabular shell at a predetermined distance from the inner surface of the acetabular shell.

8. The acetabular implant system of claim 7, wherein the liner is positionable within the acetabular shell as a single, integral component.

9. An acetabular implant system, comprising:
an acetabular shell comprising a hemispherical shape and including an outer surface, an inner surface centered on an apex of the hemispherical shape, and a lip portion joining the outer and inner surfaces such that the lip portion defines an outermost edge of the acetabular shell, the lip portion further defining an opening of the acetabular shell, the lip portion spaced from the apex by a first distance along a shell axis that extends transverse to the apex;
a liner having an inner bearing surface and an edge portion, the edge portion including an outer edge surface opposite the inner bearing surface, wherein the liner is positionable within the acetabular shell as a single, integral component; and
a fitting ring having an alignment portion and an engagement portion located radially inward of the alignment portion, the engagement portion extending circumferentially around an inner surface of the fitting ring and engageable to the outer edge surface of the liner such that the alignment portion extends radially outward from the edge portion of the liner;
wherein the engagement portion is a snap fit feature; and
wherein the alignment portion is engageable to the lip portion of the acetabular shell such that the engagement portion is spaced from the apex by a second distance along the shell axis that is greater than the first distance, thereby positioning the liner within the opening at a predetermined distance from the inner surface of the acetabular shell.

10. The acetabular implant system of claim 9, wherein the liner comprises a rigid material.

11. The acetabular implant system of claim 10, wherein the rigid material comprises at least one of a ceramic, a metal, or a composite.

12. The acetabular implant system of claim 9, wherein the fitting ring comprises a flexible material such that applying a driving force to the liner flexes the engagement portion to release the liner.

13. The acetabular implant system of claim 9, wherein the acetabular shell includes a taper portion between the inner surface and the lip portion, and wherein the taper portion has a different curvature than the inner surface.

14. The acetabular implant system of claim 9, wherein a diameter of the fitting ring corresponds to a diameter of the acetabular shell such that the alignment portion engages the lip portion of the acetabular shell when the liner is inserted into the opening.

15. The acetabular implant system of claim 9, wherein the fitting ring extends over and radially inward of the edge portion of the liner.

* * * * *